United States Patent
Ferek-Petric

(10) Patent No.: US 7,526,335 B2
(45) Date of Patent: Apr. 28, 2009

(54) COMMUNICATIONS SYSTEM FOR AN IMPLANTABLE DEVICE AND A DRUG DISPENSER

(75) Inventor: Bozidar Ferek-Petric, Zagreb (HR)

(73) Assignee: Medtronic, Inc., Minneapolis, MN (US)

(*) Notice: Subject to any disclaimer, the term of this patent is extended or adjusted under 35 U.S.C. 154(b) by 626 days.

(21) Appl. No.: 11/077,269

(22) Filed: Mar. 10, 2005

(65) Prior Publication Data
US 2006/0206067 A1 Sep. 14, 2006

(51) Int. Cl.
*A61N 1/36* (2006.01)
(52) U.S. Cl. .................. 607/3; 607/27; 607/28
(58) Field of Classification Search .............. 607/3; 604/890.1, 891.1
See application file for complete search history.

(56) References Cited

U.S. PATENT DOCUMENTS

| | | | |
|---|---|---|---|
| 4,360,125 A | | 11/1982 | Martindale et al. |
| 5,710,551 A | | 1/1998 | Ridgeway |
| 5,817,131 A | * | 10/1998 | Elsberry et al. ............... 607/5 |
| 5,925,066 A | * | 7/1999 | Kroll et al. .................... 607/3 |
| 6,045,513 A | * | 4/2000 | Stone et al. ................ 600/508 |
| 6,250,309 B1 | | 6/2001 | Krichen et al. |
| 6,418,346 B1 | | 7/2002 | Nelson et al. |
| 6,442,433 B1 | | 8/2002 | Linberg |
| 6,471,645 B1 | | 10/2002 | Warkentin et al. |
| 6,480,745 B2 | | 11/2002 | Nelson et al. |
| 6,574,511 B2 | | 6/2003 | Lee |
| 6,599,250 B2 | | 7/2003 | Webb et al. |
| 7,130,695 B2 | * | 10/2006 | Czygan et al. ................ 607/59 |
| 2002/0087113 A1 | * | 7/2002 | Hartlaub ...................... 604/65 |
| 2002/0099328 A1 | * | 7/2002 | Scheiner et al. .............. 604/67 |
| 2005/0144038 A1 | * | 6/2005 | Tamblyn et al. ................ 705/2 |

FOREIGN PATENT DOCUMENTS

| | | |
|---|---|---|
| WO | WO0149364 A2 | 7/2001 |
| WO | WO02074386 A1 | 9/2002 |
| WO | WO2005009514 A2 | 2/2005 |

* cited by examiner

*Primary Examiner*—Kennedy J Schaetzle
(74) *Attorney, Agent, or Firm*—Stephen W. Bauer; Scott A. Bardell

(57) ABSTRACT

A system for monitoring drug dispensation and drug effects on physiological signals or implantable medical device (IMD) performance is provided. The system includes a drug dispenser adapted for telemetric communication with an IMD, an IMD capable of acquiring time-based physiological or device performance data, and a programmer/monitor for receiving and displaying IMD-acquired data and drug dispensation data. The system may further include a patient activator for transmitting signals indicative of symptoms experienced by a patient associated with a side-effect caused by a drug or a condition for which the drug has been prescribed to treat. In an associated method, a drug dispensation signal is generated upon activation of the drug dispenser. IMD-acquired data, drug dispensation data, and patient symptom data are retrieved by a programmer/monitor. IMD-acquired data is combined with or grouped according to drug dispensation data and displayed.

20 Claims, 8 Drawing Sheets

COMMUNICATIONS SYSTEM FOR AN IMPLANTABLE DEVICE AND A DRUG DISPENSER

RELATED APPLICATIONS

This application is related to U.S. Patent Application filed Mar. 10, 2005, entitled "A Communications System for an Implantable Device and a Drug Dispenser").

FIELD OF THE INVENTION

The present invention relates to implantable medical devices and particularly to an implantable medical device system having communication with a drug dispenser for monitoring drug dispensation and for monitoring physiological effects of the drug.

BACKGROUND OF THE INVENTION

A patient having an implantable medical device (IMD) to monitor physiological conditions or provide therapies is often medicated for treating the same or other medical conditions. As is often the case, patients may take a variety of medications, which may have varying interactions and may impact the physiological response to the operation and functional parameters of the IMD or on physiological signals being monitored by the IMD.

The compliance of patients in following a drug regimen is often uncertain. The occurrence of symptoms or side effects related to a particular drug or a medical condition being treated by the drug may be poorly documented. Drug dispensing systems with alert features to monitor and manage the administration of medication have been proposed. For example, a medication dispenser including a medication alert signal provided in accordance with a desired medication regimen is generally disclosed in U.S. Pat. No. 4,360,125 issued to Martindale, et al.

Communication technology applied in implantable medical device systems allow remote patient management in that a clinician may monitor data acquired by an IMD as well as program IMD operating parameters from a significant distance. Remote patient management is likely to be come more prevalent as technology to enable safe remote patient care emerges.

BRIEF SUMMARY OF THE INVENTION

In general, the invention is directed to an IMD system for monitoring drug dispensation and monitoring drug effects on physiological signals or IMD performance. Medication regimens may impact a patient's response to IMD delivered therapies and vice versa. A clinician may review IMD-acquired physiological data and IMD performance data and make programming changes, either locally or remotely. The present invention provides drug dispensation monitoring in addition to available monitoring of IMD-acquired physiological signals or IMD performance. The clinician may review changes in physiological data or IMD performance that occur relative to drug dispensation events. Changes in drug regimes and/or IMD operating parameters may be made accordingly.

In one embodiment of the invention, a system includes an IMD, a drug dispenser adapted to communicate with the IMD, and a processor and memory implemented in the IMD for acquiring and storing data over time. Data acquired and stored by the IMD may include device performance data and/or physiological signal data. The drug dispenser includes a drug-releasing member, which when activated by a patient, causes the drug dispenser to transmit a communication signal to the IMD. The transmitted signal includes data corresponding to the type of drug dispensed. A time and date stamp may be applied by the drug dispenser upon transmission or by the IMD upon receipt of the drug dispensation signal.

In another embodiment, the system includes a patient activator adapted for communicating with an IMD. The patient activator provides buttons corresponding to specified symptoms, which may be symptoms commonly, experienced in association with the patient's prescribed medications. Upon activation of a button, the patient activator transmits a communication signal to the IMD corresponding to the type of symptom being experienced.

In another embodiment, the system further includes a local programmer/monitor adapted for bidirectional communication with the IMD. The local programmer/monitor is coupled to a communications network to allow data to be transferred to or from a remote programmer/monitor to allow a clinician to remotely review IMD acquired data with drug dispensation data and patient symptom data.

In another embodiment, the invention is directed to a method for storing IMD-acquired data with time-related drug dispensation data received from a drug dispenser and/or symptom data received from a patient activator. The stored data is transferred to a programmer/monitor for display to a clinician. Data is displayed in a relevant manner wherein drug dispensation data is displayed with IMD-acquired data that may be influenced by the type of drug dispensed. The display may include time-based graphs with symbols or notations indicating the time of drug dispensation and/or symptoms relative to the IMD-acquired data. The display may alternatively include graphs of IMD-acquired data grouped according to drug dispensation data.

DETAILED DESCRIPTION

The invention pertains to an IMD system for monitoring drug dispensation. Drug interactions and physiological effects can impact physiological signals monitored by an IMD and the patient's response to therapies delivered by the IMD. The invention provides for monitoring the time of drug dispensation so that drug dispensation data may be reviewed relative to other physiologic or device performance data acquired by the IMD. The invention provides for the display of time-based IMD acquired data with the temporal relation of drug dispensation events indicated by symbol or notation. The clinician is able to obtain a whole picture of monitored physiological signals, device delivered therapies and the response thereto, and drug regime effects. The clinician is better informed for making changes to a drug regime and IMD operation for the greater benefit of the patient.

Figure 1:
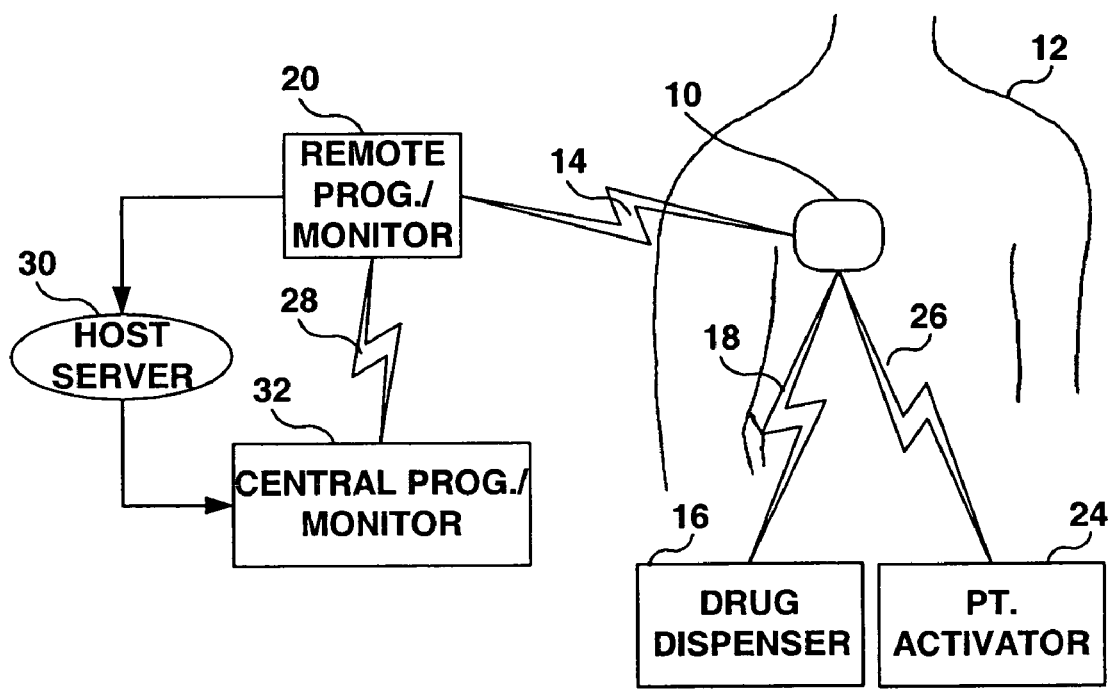
FIG. 1 is a block diagram illustrating an IMD system that provides for drug-dispensation monitoring.

FIG. 1 is a block diagram illustrating an IMD system that provides for drug-dispensation monitoring. The system includes an IMD 10 implanted in a patient 12, a drug dispenser 16 adapted for communicating with IMD 10 via telemetry link 18, and a remote programmer/monitor 20 adapted for communicating with IMD 10 via telemetry link 14. Remote programmer/monitor 20 may be adapted for communicating with IMD 10 using long-range or short-range telemetry systems and is located proximate the IMD, within telemetry range, during telemetry sessions. Programming commands or interrogation requests are transmitted from remote programmer/monitor 20 to IMD 10.

Drug dispensation signals are transmitted from drug dispenser 16 to IMD 10 via link 18. Drug dispensation signals indicate the type of drug dispensed and may include a time/date stamp indicating when the drug was dispensed. Alternatively, a time/date stamp may be applied by IMD 10 upon receipt of a drug dispensation signal from drug dispenser 16.

Typically, patient 12 will be proximate drug dispenser 16 at the time that a drug is dispensed in response to activation by patient 12. As such, drug dispenser 16 will be in telemetry range of IMD 10 allowing link 18 to be established for transmitting a drug dispensation signal from drug dispenser 16 to IMD 10.

In other embodiments, drug dispenser 16 may be enabled to communicate with remote programmer/monitor 20 via communication link 18'. Communication link 18' may be a hardwired or wireless communication link. Drug dispenser 16 may transmit drug dispensation signals to remote programmer/monitor 20 via link 18'. Transmission of drug dispensation signals to remote programmer/monitor 20 may be performed if drug dispenser 16 is out of telemetry range of IMD 10 or telemetry link 18 cannot be established due to interference or other causes. In some situations, patient 12 may not be the person receiving a drug from drug dispenser 16. and as a result IMD 10 may be out of telemetry range of drug dispenser 16 at the time of drug dispensation and signal transfer. Transfer of drug dispensation signals to remote programmer/monitor 20 may be the preferred implementation in some embodiments so as to reduce the memory burden on IMD 10 for storing drug dispensation data.

Remote programmer/monitor 20 may function as a communication interface between IMD 10 and a central programmer/monitor 32. Central programmer/monitor 32 is included in a remote patient management system that enables continuous or periodic monitoring of patients either in a remote hospital setting or in a home environment. Data acquired by IMD 10 can be transferred to remote programmer/monitor 20 through telemetry link 14. Remote programmer/monitor 20 is coupled to a communication network 28 to allow transfer of data received from IMD 10 to the central programmer/monitor 32. Likewise, remote programmer/monitor 20 may receive programming data from the central programmer/monitor 32 via communication network 28. Remote programmer/monitor 20 forwards the programming data to IMD 10 via telemetry link 14. Communication network 28 may be a local area network, a wide area network, a telecommunications network or other appropriate communications network and may be established using wireless communications.

Transfer of data between remote programmer/monitor 20 and central programmer/monitor 32 may occur via a networked host server 30, which may provide device data conversion service. Other examples of communication schemes that may be used in remote monitoring systems are generally disclosed in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al., all of which patents are incorporated herein by reference in their entirety.

Central programmer/monitor 32 includes an associated database for storing medical records and programs or algorithms for analyzing and presenting medical data. Central programmer/monitor 32 may further include a processor for converting data to or from a device format. Alternatively, as noted above data conversion may be performed by host server 30. To facilitate programming operations, a graphical user interface may be used for viewing and selecting programming options and commands to be transferred to IMD 10. Central programmer 32 may be implemented on a computer located at a clinic or implemented on the Internet, accessible using a web browser.

In an exemplary embodiment, drug dispensation data received by IMD 10 from drug dispenser 16 is incorporated with other IMD-acquired data for transmission to remote programmer/monitor 20. Such data may then be displayed by remote programmer/monitor 20 or transferred to central programmer/monitor 32 such that it is available for display and further analysis for use in remote patient management. A clinician is able review the patient's drug intake schedule based on dispensation data and observe any impact of drug intake on physiological signals and/or device function over time.

In other embodiments, remote programmer/monitor 20 receives drug dispensation data from drug dispenser 16 and IMD-acquired data from IMD 10. Drug dispensation data and IMD-acquired data may be combined and displayed by remote programmer/monitor 20 or transferred to central programmer/monitor 32 for display. In other alternative embodiments, drug dispenser 16 is coupled to a communication network 19 for transferring drug dispensation data directly to central programmer/monitor 32. Communication network 19 may be a local area network, a wide area network, a telecommunications network or other appropriate communications network and may be established using wireless connections. IMD-acquired data received by central programmer/monitor 32 via remote programmer/monitor 20 is combined with drug dispensation data for display and analysis fur use in remote patient management.

The system may further include a patient activator 24. Patient activator 24 is adapted for short-range or long-range telemetry communication with IMD 10 via telemetry link 26. Patient activator 24 provides buttons corresponding to drug-related symptoms. Upon experiencing a drug-related symptom, patient 12 may activate a corresponding button provided on patient activator 24. Patient activator 24 transmits a signal to IMD 10 in response to patient activation of a symptom button. The transmitted signal indicates the type of symptom being experienced by the patient. A time and date stamp may be applied by patient activator 24 or IMD 10 to indicate when the patient experienced the symptom. Symptom data received by IMD 10 from patient activator 24 may be transferred to remote programmer/monitor 20. Symptom data may be incorporated with other IMD-acquired data such that the time relation of symptom occurrence relative to other time-based physiological or device performance data can be known. The occurrence of symptom data relative to drug-dispensation data transmitted by drug dispenser 16 may also be ascertained.

Figure 2:
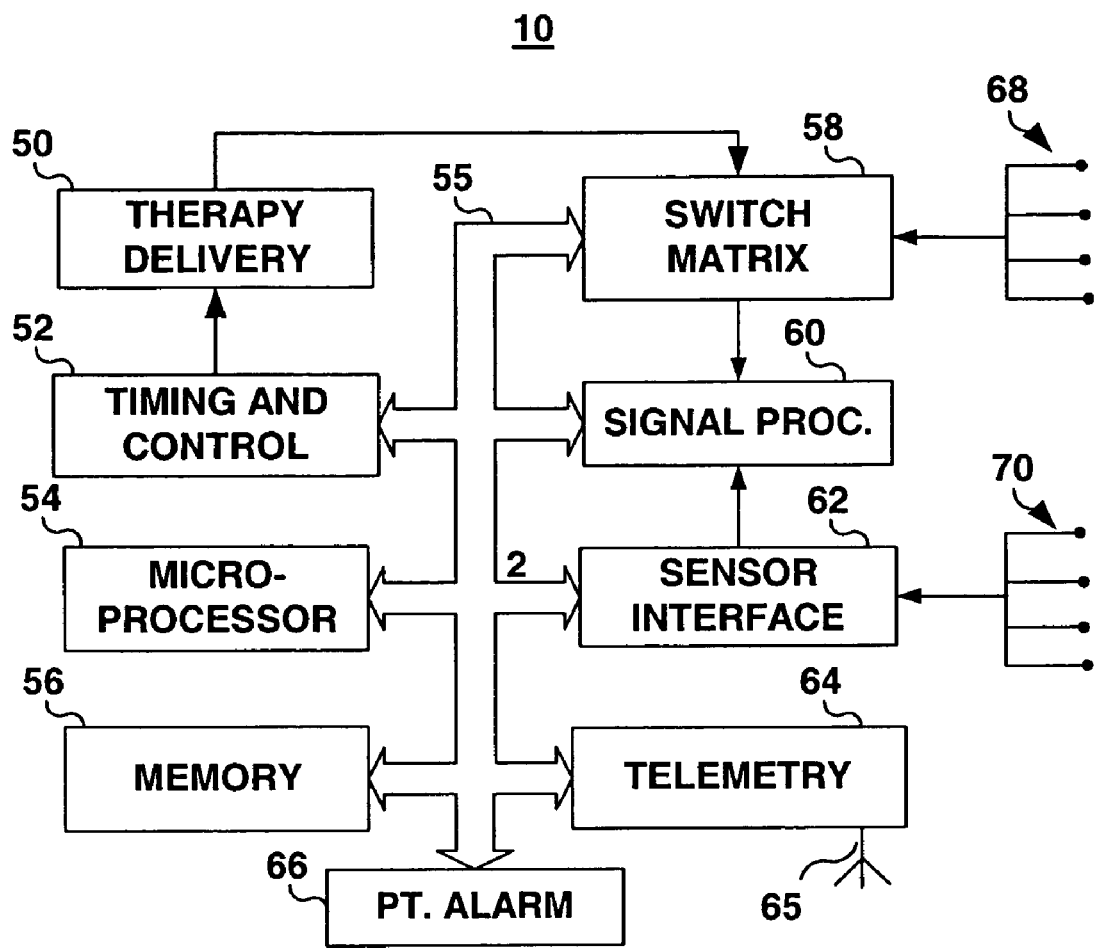
FIG. 2 is a block diagram of typical functional components of an IMD, such as the IMD shown in FIG. 1.

FIG. 2 is a block diagram of typical functional components of an IMD, such as the IMD shown in FIG. 1. IMD 10 generally includes timing and control circuitry 52 and an operating system that may employ microprocessor 54 or a digital state machine for timing and controlling sensing and therapy delivery functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control unit 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog-to-digital converter. Electrodes 68 may also be used for sensing electrical signals within the body, such as cardiac signals, neural signals, electromyogram signals, or for measuring impedance. In the case of cardiac stimulation devices, cardiac electrical signals are sensed for determining when an electrical stimulation therapy is needed and in controlling the timing of stimulation pulses. In other embodiments, electrodes 68 may be used for measuring impedance signals for monitoring, for example, edema, respiration or heart chamber volume.

IMD 10 may additionally or alternatively be coupled to one or more physiological sensors 70. Such sensors may include pressure sensors, accelerometers, flow sensors, blood chemistry sensors, activity sensors or other physiological sensors known for use with IMDs. Sensors 70 are coupled to IMD 10 via a sensor interface 62, which provides sensor signals to signal processing circuitry 60. Sensor signals are used by microprocessor 54 for detecting physiological events or conditions. For example, IMD 10 may monitor heart wall motion, blood pressure, blood chemistry, respiration, or patient activity. Monitored signals may be used for sensing the need for delivering a therapy under control of the operating system. Physiological data may be recorded continuously by IMD 10 or upon a detected triggering event or change in a monitored physiological condition. Acquired physiological data can be stored for later transfer to an external programmer/monitor or transferred in real-time.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. All of these functions and operations are known in the art, and many are generally employed to store operating commands and data for controlling device operation and for later retrieval to diagnose device function or patient condition. Microprocessor 54 controls device diagnostic functions, such as lead impedance monitoring, stimulation threshold testing, and device longevity estimation. Microprocessor 54 may also manage the storage of device performance parameters such as pacing capture success rate, frequency of delivered therapies, and response to delivered therapies. Device-related parameters acquired by IMD 10 may be transferred to an external programmer for evaluating device function.

Microprocessor 54 may be programmed to generate an alert or alarm notifications in response to detecting predetermined physiological or device-related conditions or events. A patient alert signal is generated by patient alarm circuitry 66. A patient alert signal may be an audible sound or a perceivable vibration or other sensory stimulation. A patient alert signal may notify a patient that a medication is recommended, based on a scheduled medication regime and the known time since the last drug dispensation signal was received by IMD 10. Alternatively, a patient alert signal may be generated in response to a changing physiological condition indicating the need for medication.

In some embodiments, if IMD 10 is expecting a drug dispensation signal (according to a programmed in schedule or following a patient alert signal) and does not receive one, the IMD may automatically adjust operating parameters controlling IMD monitoring or therapy delivery functions.

IMD 10 is equipped with telemetry circuitry 64 and antenna 65 for bidirectional communication with external devices. In accordance with the present invention, telemetry circuitry 64 includes telemetry circuitry for establishing a bidirectional communication link with a remote programmer/monitor 20 and a drug dispenser 16 (shown in FIG. 1). Telemetry circuitry 64 may further include circuitry for establishing a communication link with a patient activator 24 (FIG. 1). Programming data and device-related or physiological monitoring data are transmitted during downlink or uplink telemetry, respectively, between IMD telemetry circuitry 64 and external telemetry circuitry included in remote programmer/monitor 20. Drug dispensation signals are received by IMD telemetry circuitry 64 from external telemetry circuitry included in the drug dispenser 16. Drug-related symptom signals are received by IMD telemetry circuitry 64 from external telemetry circuitry included in the patient activator 24.

In an exemplary embodiment, telemetry circuitry 64 and antenna 65 are implemented as a long range telemetry system, which allows communication between IMD 10 and an external device (programmer/monitor 20, drug dispenser 16, or patient activator 24) to occur without the use of a programming head or wand as required in short-range telemetry systems. Telemetry circuitry 64 and antenna 65 may be tuned to establish bidirectional communication with each external device, programmer 20, drug dispenser 16, and patient activator 24, using the same transmission frequency. Alternatively, telemetry circuitry 64 and antenna 65 may include separate circuits and antennae tuned for communicating individually with the external devices (programmer 20, drug dispenser 16, and patient activator 24) at different transmission frequencies.

Figure 3:
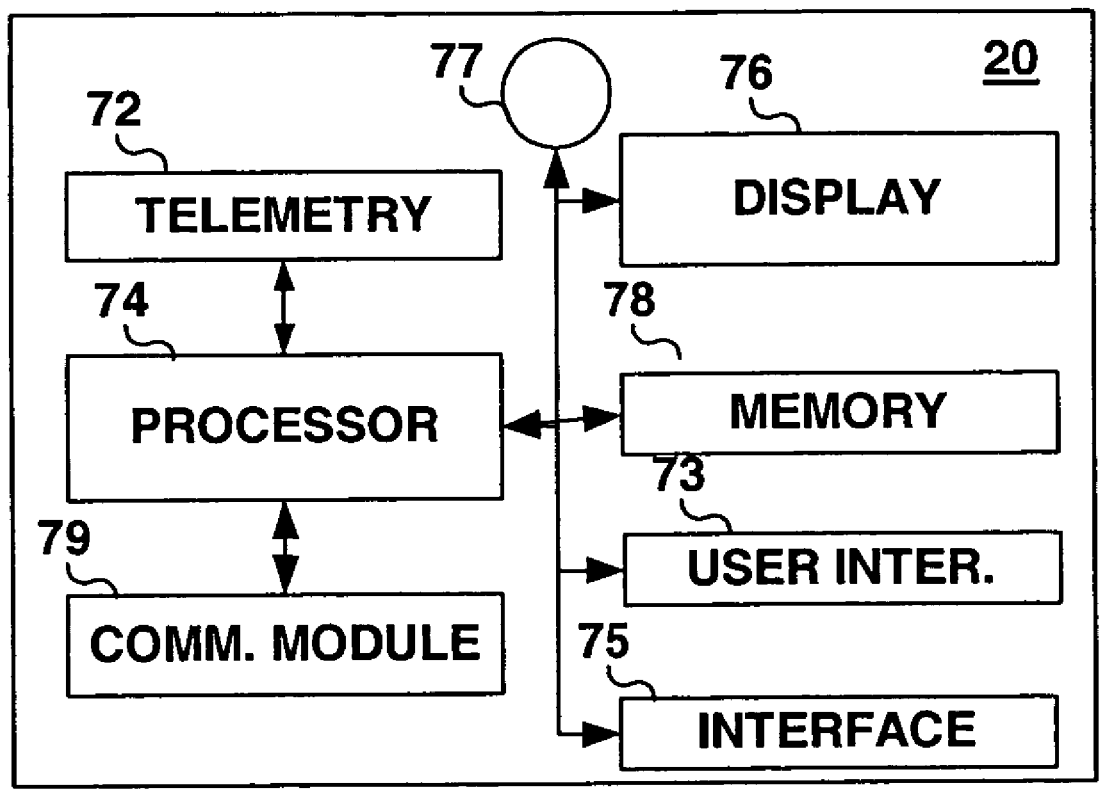
FIG. 3 is a functional block diagram of typical components included in a remote programmer used in programming an IMD, such as the remote programmer shown in FIG. 1.

FIG. 3 is a functional block diagram of typical components included in a remote programmer used in programming an IMD, such as remote programmer 20 shown in FIG. 1. Remote programmer 20 is located at a remote location, such as a patient's home or in a clinic or other medical facility away from the central patient management system. Remote programmer 20 includes a communication network interface 79, which may be embodied as a modem, used for communicating with a central programmer/monitor. Remote programmer 20 acts as communication conduit between the central programmer and an IMD. Remote programmer 20 transfers programming data received from the central programmer/monitor to the IMD. Remote programmer 20 also transfers data retrieved from the IMD to the central programmer/monitor.

Remote programmer/monitor 20 shown in FIG. 3 includes a telemetry circuit 72 for bidirectional communication with IMD 10 shown in FIG. 1. Telemetry circuit 72 may also be adapted to receive drug dispensation signals from drug dispenser 16. Remote programmer 20 includes a processor 74 operating with associated memory 78 for controlling programmer/monitor functions. Memory 78 may be used to store IMD-acquired data received from IMD 10 and drug dispensation data received either from IMD 10 or directly from drug dispenser 16. Remote programmer/monitor may perform data processing so as to combine IMD-acquired data with relevant drug dispensation data and patient symptom data. Remote programmer/monitor may transfer raw or processed IMD-acquired data, drug dispensation data and patient symptom data to central programmer/monitor 32 (FIG. 1). Alternatively or additionally, all or a portion of the data may be displayed by remote programmer/monitor 20.

Display 76 may be provided to display IMD-acquired data, drug dispensation data, patient symptom data, or other patient related data as well as menu choices and data entry fields used for entering commands or parameters during a telemetry session. Display screen 76 may display a variety of screens of retrieved IMD data, previously stored or in real time and may display uplinked event signals as they are received and thereby serve as a means for enabling the user to timely review IMD operating history and status. Display 76 may be used for displaying messages to a patient regarding the status of a drug regime and drug dispensation data.

A speaker 77 may be provided for broadcasting audible tones or messages used to alert the user of the status of programmer/monitor functions or patient-related conditions. In order for a clinician, patient, or caregiver to interact remote programmer 20, a keyboard, graphical user interface, or other user interface 73, coupled to processor 74, is provided. Display 76 and/or the user interface 73 allow a user to enter command signals to initiate transmissions of downlink or uplink telemetry and to initiate and control telemetry sessions once a telemetry link with an implanted device has been established. Other types of user interaction mechanisms and electronics may be implemented such as voice recognition/response systems. Remote programmer 20 may further include an interface 75 for coupling peripheral devices, which may include external monitoring equipment such as ECG leads, blood pressure monitor, etc.

Figure 4:
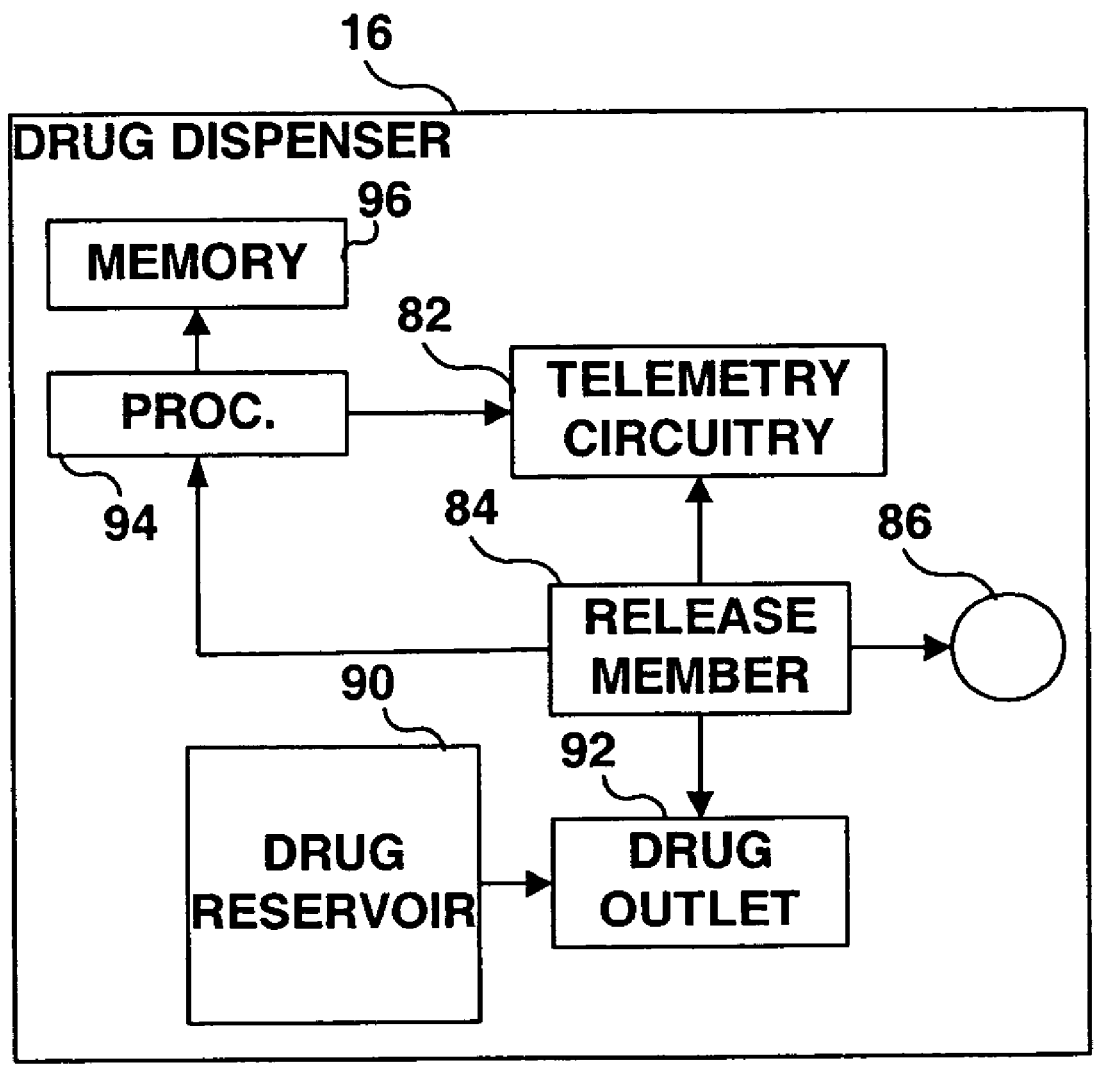
FIG. 4 is a block diagram illustrating major components included in a drug dispenser.

FIG. 4 is a block diagram illustrating major components included in drug dispenser 16. A drug reservoir 90 is provided for containing a medication, which may be in tablet or liquid form. A release member 84 is provided for activation by a patient or caregiver to cause medication held in reservoir 90 to be released through drug outlet 92. A patient feedback element 86 may be included to provide the patient with sensory feedback when release member 84 is properly activated. Patient feedback element 86 may generate an audible sound such as a beep or tone or may be embodied as an LED that illuminates upon proper activation of release member 84.

Activation of release member 84 additionally triggers telemetry circuitry 82 to generate a signal transmission to IMD telemetry circuitry. Typically a patient will be standing proximate drug dispenser 16 during activation of release member 84 causing drug dispenser 16 to be within telemetry communication range of IMD 10. As such, a drug dispensation signal triggered by activation of release member 84 may be transferred immediately to an IMD via telemetry circuitry 82. A drug dispensation signal may include the type of drug dispensed, the dosage dispensed and the time and date of dispensation.

Patient feedback element 86 may be used to generate a sensory signal notifying the patient of a signal transmission status. A successful or unsuccessful transmission may be indicated to the patient via unique tones or LED colors. If the transmission is unsuccessful, the patient may adjust his/her position relative to drug dispenser 16 to allow successful signal transmission to take place.

In some embodiments, drug dispenser telemetry circuitry 82 may be adapted for communicating directly with remote programmer/monitor 20. Drug dispenser 16 may be located within communication range of programmer/monitor 20 and transmit a drug dispensation signal to programmer/monitor 20 upon activation of release member 84. Programmer/monitor 20 would store drug dispensation data, which may include the type of drug and a time/date stamp applied by either drug dispenser 16 or programmer/monitor 20. When programmer/monitor 20 receives data acquired from IMD 10, the IMD data and drug dispensation data can be combined to provide a display incorporating drug dispensation events relative to time-based IMD data.

Since patients are often medicated with more than one drug, multiple drug dispenser units may be provided. Multiple drug dispenser units may each include each of the components described in FIG. 4. Alternatively, multiple drug dispensing units may share one or more components. For example, a separate drug reservoir 90 would be provided for each type of drug, but the drugs may be released into a common drug outlet 92 with patient feedback provided by a common patient feedback element 86. An individual release member 84 would be provided for each drug to allow the patient to select the drug to be released. Release member 84 may then trigger a unique signal for transmission by telemetry circuitry 82 corresponding to the type of drug released.

In one embodiment, drug dispenser 16 is color coded to match the color of the type of drug being dispensed. Patients taking multiple drugs often distinguish the drugs according to the color of the tablets. Drug dispenser 16 may be colored corresponding to the color of the tablets being dispensed. The signal transmitted by telemetry circuitry 82 upon activation of release member 84 may be coded according to the color of the drug, the name of the drug, an assigned number, or other drug indicator.

In some embodiments, drug dispenser 16 may be a standalone device adapted for communicating with IMD 10. In other embodiments, drug dispenser 16 may be incorporated in remote programmer/monitor 20, in which case the telemetry circuitry included in remote programmer/monitor 20 may be used for transmitting drug dispensation signals to IMD 10. Alternatively, drug dispensation data may be stored by remote programmer/monitor 20 so that it may be combined with data retrieved from IMD 10 for display or transfer to a central programmer/monitor.

Drug dispenser 16 may optionally include control circuitry such as processor 94 and associated memory 96 for use in managing a medication regime. A clinician may program the schedule for taking prescribed medications. Processor 94 may trigger patient feedback element 86 to generate signals to remind a patient to take a scheduled medication.

In yet other embodiments, drug dispenser 16 may include memory 96 under the control of processor 94 for storing drug dispensation data. The time and date and type of drug dispensed may be stored in memory 96 upon activation of release member 84. The drug dispensation data stored in memory 96 may be transferred to either an IMD or a programmer/monitor via telemetry circuitry 82. Transfer of drug dispensation data may occur in response to an interrogation command, at a scheduled time, or upon detection of a received telemetry signal strength indicating drug dispenser 16 is within telemetry range of IMD 10 or remote programmer/monitor 20. Storage of drug dispensation data for later transfer to an IMD or programmer/monitor is useful in situations wherein the patient is not the person dispensing the drug or a telemetry link is not established at the time of drug dispensation due to interference or other causes.

Figure 5:
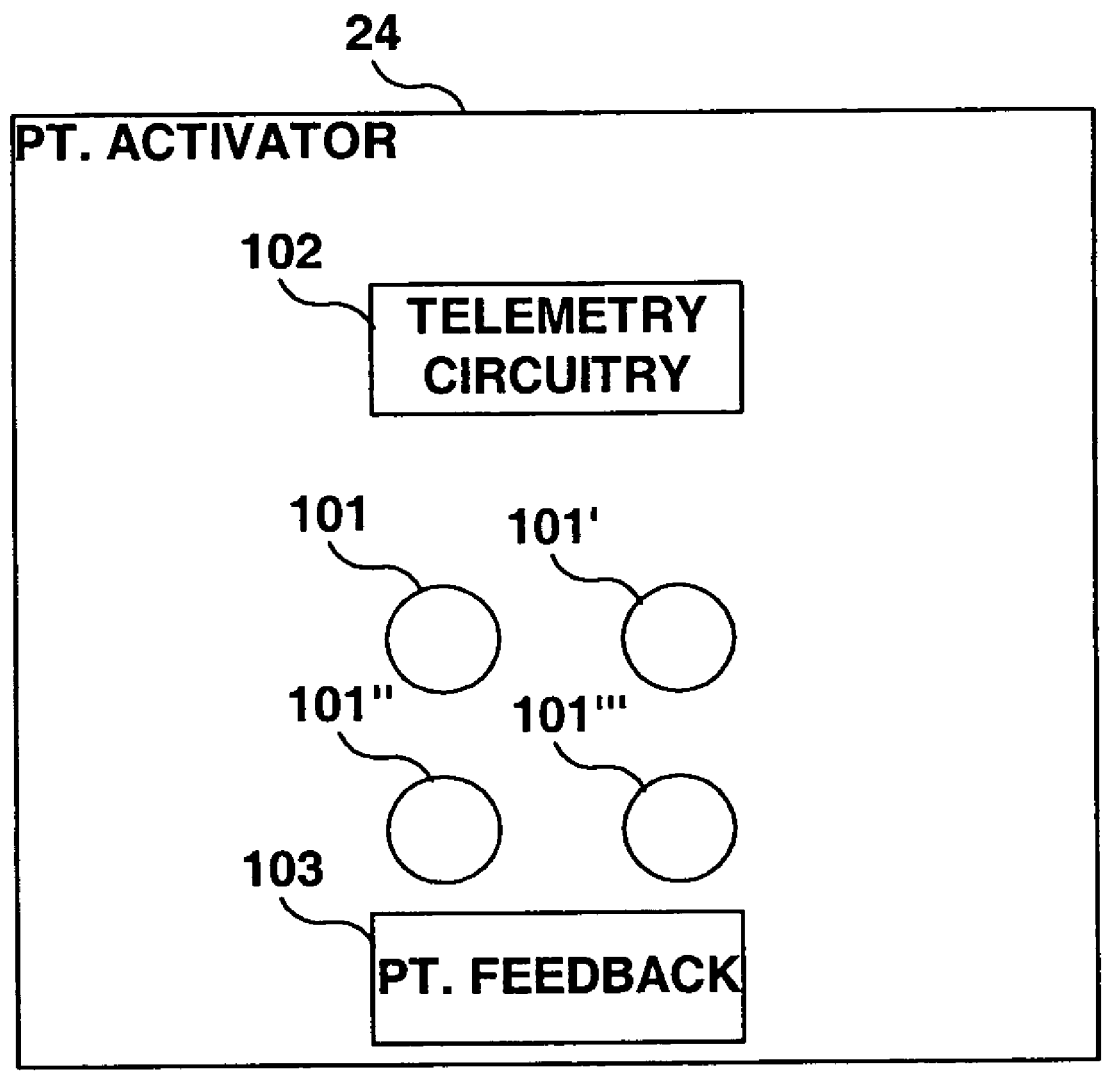
FIG. 5 is an illustration of a patient activator that may be used for transferring patient symptom data to an IMD.

FIG. 5 is an illustration of a patient activator that may be used for transferring patient symptom data to an IMD. Patients may experience symptoms related to a physiological condition or related to drug side-effects. For example, a patient may experience nausea, vomiting, dyspnea, palpitations, dizziness, syncope, or other symptoms. A patient activator 24 may be provided having one or more buttons 101, 101', 101" and 101'" corresponding to a particular symptom. The patient may press the appropriate button 101, 101', 101" or 101'" upon experiencing a symptom or side-effect. In response to a button being pressed, telemetry circuitry 102 included in patient activator 24 will transfer a signal to IMD 10. The transferred signal communicates data indicative of the experienced symptom. A time and date stamp may be included in the transferred signal or applied by IMD 10 upon receipt of the transferred signal. A record of symptomatic events may then be stored by IMD 10 so that it is available for display relative to drug dispensation data and/or other time-based data acquired by IMD 10. Upon review of such data, a clinician may observe correlation between patient symptoms and a prescribed drug regime and/or physiological conditions or events.

In one embodiment, buttons 101, 101', 101" and 101'" are color coded to correspond to the color of a prescribed medication, which may further correspond to the color of a drug dispenser used for dispensing the medication. Color-coded buttons 101, 101', 101" and 101'" would represent a typical side-effect caused by the correspondingly colored medication or a symptom associated with the medical condition for which the drug has been prescribed to treat. In alternative embodiments, buttons 101, 101', 101", 101'" are coded by shape, Braille letters, icons, numbers or other symbols to correspond to particular symptoms or drugs.

Patient activator 24 may further include a patient feedback component 103 for indicating to the patient that a button 101, 101', 101", 101'" has been properly depressed. Patient feedback component 103 may be an LED that illuminates upon depression of one of buttons 101, 101', 101", 101'". Alternatively, patient feedback component 103 may be embodied as a sound-emitting element that generates an audible sound upon depression of one of buttons 101, 101', 101", 101'".

Patient activator 24 will typically be adapted for transferring signals to IMD 10 since generally the patient using activator 24 can conveniently hold activator 24 within telemetric range of IMD 10. In alternative embodiments, patient activator 24 may be enabled to communicate with drug dispenser 16 and/or remote programmer/monitor 20. Drug dispenser 16 may acquire and store symptom data and transfer such data with drug dispensation data to IMD 10 or remote programmer/monitor 20. Programmer/monitor 20 may receive symptom data from patient activator 24 and store the symptom data for later incorporation with drug dispensation data received from IMD 10 or drug dispenser 16 or other time-based physiological or device performance data received from IMD 10.

Figure 6:
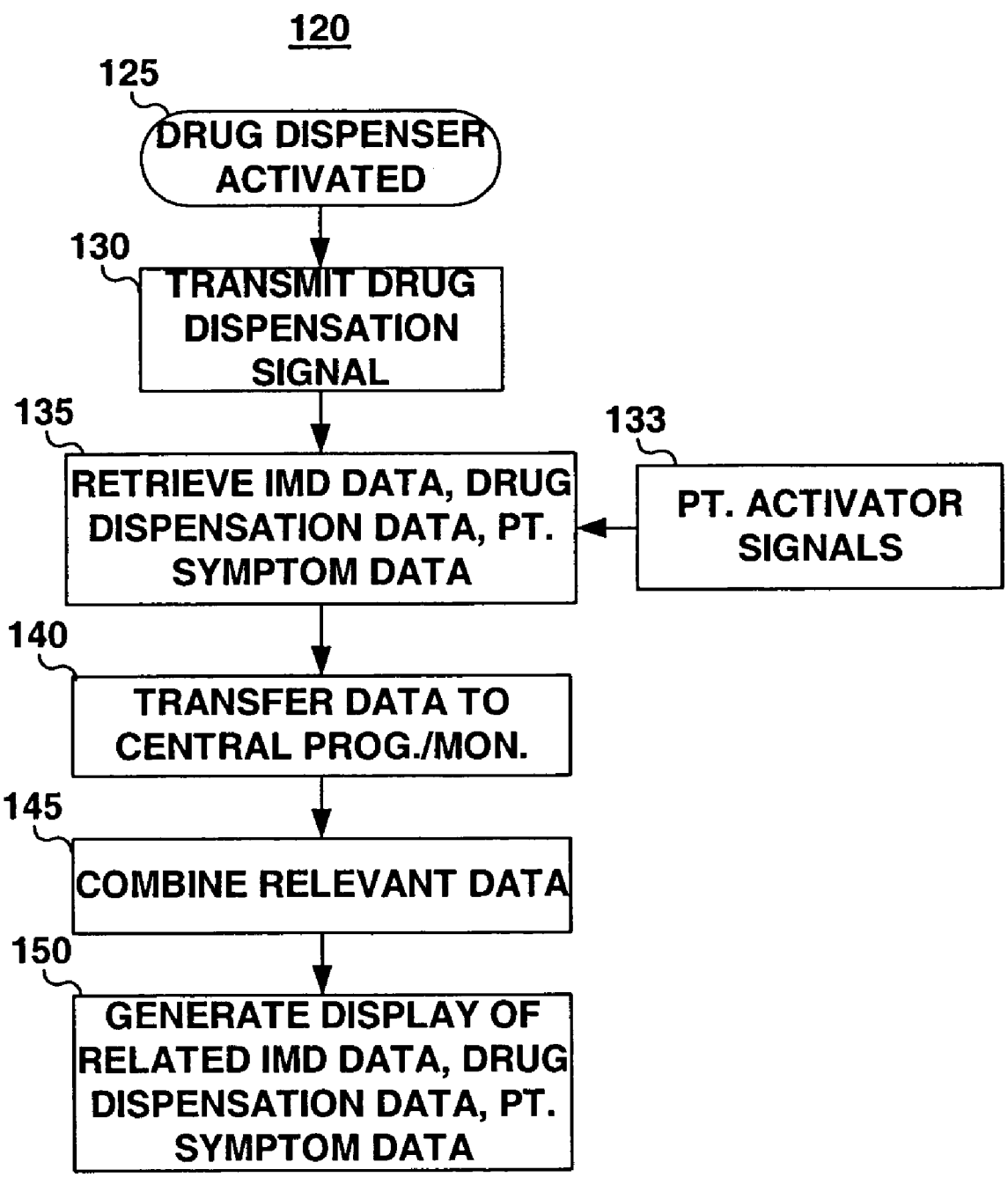
FIG. 6 is a flow chart summarizing steps included in a method for monitoring drug dispensation and symptoms according to one embodiment of the invention.

FIG. 6 is a flow chart summarizing steps included in a method for monitoring drug dispensation and symptoms according to one embodiment of the invention. At step 125, drug dispenser 16 is activated to release a medication. Upon activation, a drug dispensation signal is transmitted at step 130 from drug dispenser 16 to IMD 10. The drug dispensation signal may indicate the type of drug dispensed, the dosage dispensed, and the time and date of dispensation. As described previously, drug dispensation signals may alternatively be stored by drug dispenser 16 for a period of time and transferred to IMD 10 whenever a telemetry link is established or at scheduled transmission times. Drug dispensation signals may alternatively be transferred to a remote programmer/monitor 20 rather than IMD 10.

At step 133, patient activator signals may be transferred to IMD 10 when a patient uses patient activator 24 as described previously. Alternatively patient activator signals may be received by drug dispenser 16 or remote programmer/monitor 20.

At step 135, remote programmer/monitor 20 retrieves data from IMD 10. Retrieved data will include drug dispensation data received by IMD 10, patient symptom data received by IMD 10 and other IMD-acquired data. IMD acquired data may include physiological events or signals and/or device performance data. Physiological events or signals may relate to, for example, blood pressure, heart wall motion, ECG signals, heart rate, arrhythmia events, blood chemistry, activity, patient position, respiration, lung wetness, EEG signals, or EMG signals. Device performance data may relate to delivered therapies, automatic device diagnostics or testing results, or automatic changes in device operating parameters. Device performance data may include, for example, frequency of cardiac pacing, pacing mode, frequency of mode switching, frequency of arrhythmia detections, arrhythmia therapies delivered and corresponding success rate, pacing capture detection rate, pacing threshold, or drug pump dosages.

At step 140, drug dispensation data, patient symptom data, and IMD acquired data may be transferred from remote programmer/monitor 20 to a central programmer/monitor 32 for analysis and display. Transfer to a central programmer/monitor 32 may be executed via a host server providing data conversion operations as well as some data processing and analysis.

At step 145, IMD-acquired data, drug dispensation data, and patient symptom data are combined and integrated in a relevant manner. Drug dispensation data and patient symptom data are combined with IMD-acquired data pertaining to the type of drug dispensed. In one example, dispensation data corresponding to an anti-arrhythmic drug is combined with heart rate, arrhythmia detection and arrhythmia therapy data acquired by the IMD. More particularly, drug dispensation data relating to an atrial anti-arrhythmia drug may be combined specifically with atrial heart rate or rhythm data. Drug dispensation data relating to ventricular anti-arrhythmia drug may be combined specifically with ventricular heart rate or rhythm data. Such data may be further combined with palpitation symptom data received from patient activator 24. In another example, dispensation data corresponding to a diuretic is combined with lung-wetness data acquired by the IMD. In yet another example, dispensation data corresponding to a blood pressure medication is combined with blood pressure signal data acquired by the IMD. Thus, data processing is performed to allow a display to be generated that combines IMD-acquired data with relevant drug dispensation data. Data processing performed at step 145 for combining relevant data may be performed entirely or in part by IMD 10, remote programmer/monitor 20, host server 30 or central programmer/monitor 32.

At step 150, a display of combined IMD-acquired data, drug dispensation data and patient symptom data is generated. In some cases, the data will be displayed in a graphical format as a time-based plot of physiological or device performance signals or events. The time of drug dispensation and patient symptom events may be indicated by markers, icons, labels, or other designations allowing a clinician to observe temporal relations between physiologic events, device performance, symptoms, and drug dispensation. In one embodiment, drug dispensation and patient symptom events are indicated using color-coded markers, icons or labels that may match the correspondingly colored drug, drug dispenser, and patient activator button.

In other cases, IMD-acquired data may be grouped according to drug dispensation data. Data may then be displayed in histogram formats wherein the frequency of physiological events, device performance events or symptomatic events are plotted for a period of time corresponding to administration of a particular drug or drug dosage. Other formats for displaying IMD-acquired data relative to relevant drug dispensation and patient symptom data may be utilized such as pie charts, tables, statistical tables or charts, and so on.

Figure 7:
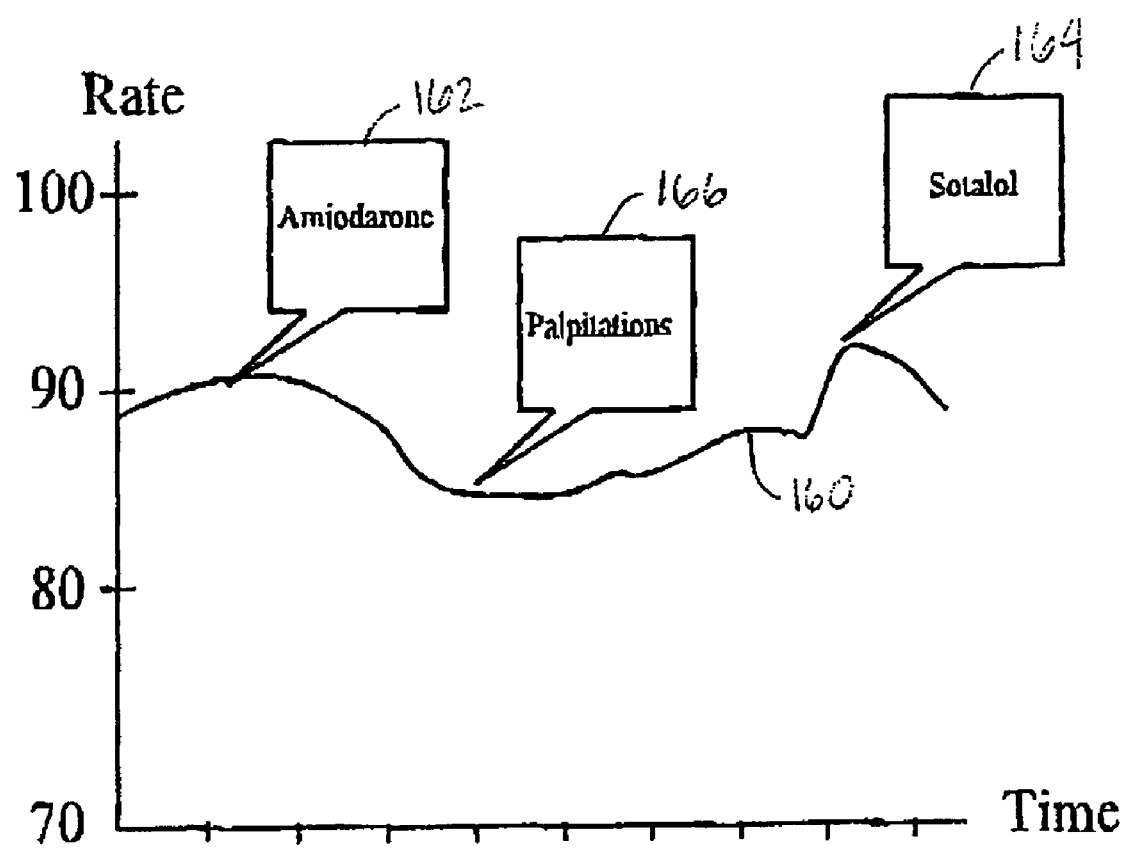
FIG. 7 is an illustration of a graphical display that may be generated using combined drug dispensation data, IMD-acquired physiologic data, and patient symptom data.

FIG. 7 is an illustration of a graphical display that may be generated using combined drug dispensation data, IMD-acquired physiologic data, and patient symptom data. In FIG. 7, heart rate measurements 160 acquired by an IMD are plotted over time. Notations indicating the time of drug dispensation events 162 and 164 are provided. A notation indicating the occurrence of a patient symptom 166 is also provided. A clinician may thus review a time-based graph of IMD-acquired physiological data combined with drug dispensation data and patient symptom data to assess the physiological response to medications. Such data presentation can be valuable to a clinician in managing both drug and IMD therapies.

Figure 8:
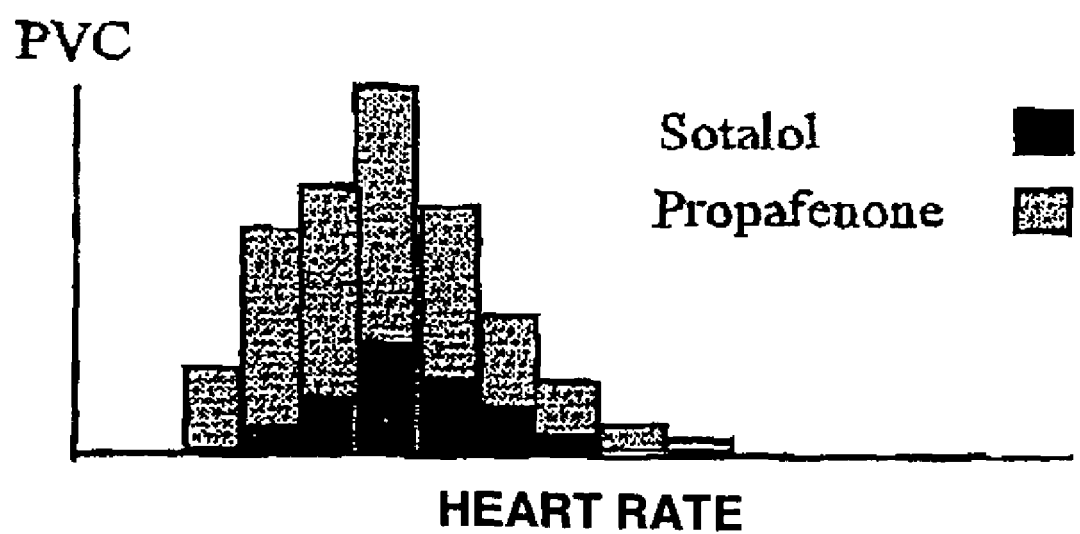
FIG. 8 is an illustration of a histogram display that may be generated using combined drug dispensation data and IMD-acquired data.

FIG. 8 is an illustration of a histogram display that may be generated using combined drug dispensation data and IMD-acquired data. Clinicians may prescribe a series of different types of drugs or drug dosages in order to identify the most effective drug regime for a particular patient. For example, patients suffering from arrhythmias may be required to undergo electrophysiologic (EP) studies for optimizing an anti-arrhythmic drug therapy. EP studies may be repeated for different drugs, drug combinations, or dosages to determine the likelihood of arrhythmias under each drug regime. Using the drug dispensation monitoring methods provided by the present invention, drug dispensation data can be combined with arrhythmia-related data acquired by an IMD for use in assessing the most effective drug regime.

In FIG. 8, the frequency of premature ventricular contractions (PVCs) detected at different heart rates is plotted. Thus, the IMD has detected PVCs and heart rate data to generate a histogram of PVC occurrence versus heart rate. In addition, drug dispensation data is collected and combined with the PVC data. In the example shown, two drugs, Sotalol and Propafenone, have been dispensed. The PVC data plotted in the display of FIG. 8 is grouped according to the drug most recently dispensed at the time of PVC data collection. Clearly, a greater number of PVCs were detected after Propafenone was dispensed than after Sotalol was dispensed in this particular example. Thus, for this hypothetical clinical case, Sotalol is more effective in controlling PVCs, a predictor of arrhythmias.

IMD-acquired physiological events or device performance events may be grouped according to a type or dosage of drug dispensed or a particular drug combination. Grouping and displaying of IMD-acquired data based on drug dispensation data can be valuable to a clinician in optimizing a drug regime.

Thus, a system and method have been described for monitoring drug dispensation and the association with drug dispensation and physiological events or IMD performance. Numerous variations to the embodiments described herein may be conceived by one having skill in the art and the benefit of the teachings provided herein. The embodiments described herein are intended to be illustrative of methods for practicing the invention and should not be considered limiting with regard to the following claims.

The invention claimed is:

1. A method, comprising:
    dispensing a drug from a drug dispenser in response to an external drug delivery activation signal;
    transmitting drug dispensation data to an implantable medical device in response to the drug dispensation;
    acquiring data through the implantable medical device indicative of a response to the dispensed drug, wherein the data includes physiological data and device performance data, the device performance data comprising implantable medical device delivered electrical stimulation therapies and a response thereto; and
    storing the drug dispensation data with the data acquired by the implantable medical device, the data acquired by the medical device grouped according to drug dispensation data.

2. The method of claim 1 wherein the drug dispensation data comprises any of the type of a drug type and a drug dosage.

3. The method of claim 2 wherein the data corresponding to the type of drug dispensed is indicative of the color of the drug dispensed.

4. The method of claim 1 wherein the drug dispensation data comprises a time and date at which the drug dispensation occurred.

5. The method of claim 1 further comprising:
    transmitting the drug dispensation data and the data acquired by the implantable medical device to a programmer/monitor;
    combining the drug dispensation data with selected implantable medical device acquired data that is responsive to the drug dispensed; and
    displaying the combined drug dispensation and implantable medical device acquired data.

6. The method of claim 5, wherein displaying the combined drug dispensation and implantable medical device acquired data comprises displaying a time-based graph of the selected implantable medical device acquired data and a symbol or notation indicative of a time of the drug dispensation.

7. The method of claim 6 wherein the symbol or notation indicative of the time of the drug dispensation is displayed in a color corresponding to the color of the drug dispensed.

8. The method of claim 5, wherein displaying the combined drug dispensation and implantable medical device acquired data includes grouping the selected implantable medical device acquired data according to any of the type of drug dispensed and the dosage of the drug dispensed.

9. The method of claim 1 wherein the drug dispensed is an anti-arrhythmia drug.

10. The method of claim 1 wherein the data acquired by the implantable medical device comprises a frequency of an implantable medical device delivered electrical stimulation therapy.

11. The method of claim 1 wherein the response to the implantable medical device delivered therapy is a rate of cardiac pacing capture success.

12. The method of claim 1 wherein the data acquired by the implantable medical device includes a physiological signal that is representative of a hemodynamic variable.

13. The method of claim 1 wherein the data acquired by the implantable medical device is a signal indicative of lung wetness.

14. The method of claim 1 wherein the implantable medical device comprises one of a cardiac stimulation device, a neurostimulator, and a drug pump.

15. The method of claim 1 further including:
   transmitting patient symptom data to the implantable medical device; and
   storing the patient symptom data with the data acquired by the implantable medical device.

16. The method of claim 15 further including:
   transmitting the stored patient symptom data and the data acquired by the implantable medical device to a programmer/monitor; and
   displaying the data acquired by the implantable medical device; and
   displaying an indication of a time and date of the patient symptom occurrence relative to the displayed implantable medical device acquired data.

17. The method of claim 16 wherein the indication is displayed in a color corresponding to the color of the drug dispensed.

18. The method of claim 1 wherein the device performance data comprises a frequency of cardiac pacing mode switching.

19. A method, comprising:
   activating a drug dispenser to deliver a drug in accordance with a treatment regimen;
   dispensing the drug from the drug dispenser in response to the activation;
   transmitting drug dispensation data to a programmer/monitor;
   acquiring data through an implantable medical device (IMD) indicative of a response to the dispensed drug, wherein the data includes physiological data and device performance data, the device performance data comprising implantable medical device delivered electrical stimulation therapies and a response thereto,
   transmitting the data acquired by the IMD to the programmer/monitor; and
   displaying the drug dispensation data and the data acquired by the implantable medical device
   the displayed data grouped according to drug dispensation data.

20. A system, comprising:
   an implantable medical device configured to acquire time-based data and deliver an electrical stimulation therapy, the time-based data comprising device performance data corresponding to the implantable medical device delivered electrical stimulation therapy and a response thereto;
   a drug dispenser adapted for telemetric communication with the implantable medical device for transferring drug dispensation data to the implantable medical device;
   a patient activator in communication with the drug dispenser, wherein the activator transmits an activation signal to the drug dispenser;
   sensing means for monitoring the time-based data indicative of a response to the dispensed drug;
   a memory for storing the drug dispensation data and the time-based data acquired by the medical device;
   a programmer/monitor adapted for telemetric communication with the implantable medical device for receiving the drug dispensation data and the implantable medical device acquired data; and
   a display for displaying the implantable medical device acquired data and the drug dispensation data, the data acquired by the medical device grouped according to drug dispensation data.

* * * * *